United States Patent [19]
Demole et al.

[11] Patent Number: 4,478,865
[45] Date of Patent: Oct. 23, 1984

[54] UTILIZATION OF SULFUR CONTAINING TERPENES AS FLAVORING INGREDIENTS

[75] Inventors: Edouard P. Demole, Coppet; Paul Enggist, Geneva, both of Switzerland

[73] Assignee: Firmenich SA, Switzerland

[21] Appl. No.: 429,087

[22] Filed: Sep. 30, 1982

Related U.S. Application Data

[62] Division of Ser. No. 331,014, Dec. 15, 1981, abandoned.

[30] Foreign Application Priority Data

Dec. 15, 1981 [CH] Switzerland .................. 9513/80

[51] Int. Cl.³ ............................................ A23L 1/235
[52] U.S. Cl. ...................................... 426/535; 568/61
[58] Field of Search ......................................... 426/535

[56] References Cited

U.S. PATENT DOCUMENTS 4,224,351  9/1980  Sundt et al. ....................... 426/535

FOREIGN PATENT DOCUMENTS 2615393 10/1976  Fed. Rep. of Germany .
1546283  5/1979  United Kingdom .

OTHER PUBLICATIONS

*Neftekhimiya,* vol. 19, No. 3, pp. 110–116 (1979), "Alkylalmuminiumdichlorides as Catalysts in the Addition of Hydrogen Sulfide to Olefins".
G. Tolstikov et al., Chem. Abstracts 91:107252q (1979).
K. Suga et al., Chem. Abstracts, 58:1495f (1963).
G. Frater et al., Chem. Abstracts, 86:120776e (1977).

*Primary Examiner*—Joseph Golian
*Attorney, Agent, or Firm*—Pennie & Edmonds

[57] ABSTRACT

Sulfur containing terpenes of formula

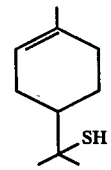

(I)

both in its racemic and enantiomeric forms possess useful organoleptic properties in developing especially fruity notes, more particularly of grapefruit character.

(S)-(−)-1-p-menthene-8-thiol and (R)-(+)-1-p-menthene-8-thiol are new compositions of matter.

3 Claims, No Drawings

UTILIZATION OF SULFUR CONTAINING TERPENES AS FLAVORING INGREDIENTS

This is a division of application Ser. No. 331,014, filed Dec. 15, 1981, now abandoned.

BRIEF SUMMARY OF THE INVENTION

The present invention relates to the field of perfumes and flavours. More particularly it relates to the use of sulfur containing terpenes of formula

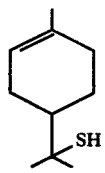

both in its racemic and enantiomeric forms of formula

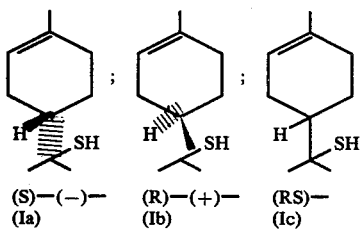

as perfuming and flavouring ingredients.

The invention provides a method to enhance, improve or modify the fragrance properties of perfumes and perfumed articles, and the flavour properties of foodstuffs, beverages, chewing gums, pharmaceutical preparations and tobacco products which method comprises the step of adding thereto an effective amount of a compound of formula (I).

This invention provides also a perfume and a flavouring composition which contain as effective ingredient a compound of formula (I).

Finally, the invention relates to novel (S)-(−)-1-p-menthene-8-thiol and (R)-(+)-1-p-menthene-8-thiol.

BACKGROUND OF THE INVENTION

The compound defined by formula (I) is 1-p-menthene-8-thiol, which in its racemic form has been described only once in the scientific literature [see: G. A. Tolstikov et al., Neftekhimiya, 19, 425–9 (1979), as reported in Chem. Abstr., 91, 107252q (1979)]. This document is however mute with regard to the organoleptic properties of the said compound and no mention nor suggestion has been made concerning its possible utility as perfumant or flavorant.

We have now discovered that compounds (I) not only possess very useful odorous and gustative qualities, but also that their properties are exceptional.

We have unexpectedly found that compounds (I) possess an unequalled strength, far higher in fact than that shown by the most powerful ingredients known so far in the art. Their perception level is of the order of the hundredthousandth of a ppb (parts per billion), more exactly of $2 \times 10^{-5}$ ppb for (R)-(+)-1-p-menthene-8-thiol and $8 \times 10^{-5}$ ppb for (S)-(−)-1-p-menthene-8-thiol. This means that significant effects can be achieved by making use of the compounds of formula (I), in accordance with the invention, at concentration as low as a few parts per billion by weight based on the total weight of the perfume or flavour compositions or articles into which they are added. It should be underlined that the positive features of compounds (I) become apparent only at very high dilution, their odour in the pure state being distinctly offensive.

It has also become apparent to us that due to the nature of their specific organoleptic properties, compounds (I) could satisfy a long lasting need, namely the faithful reconstitution of the typical taste and aroma of grapefruit juice. In terms of palatability, the commercially available compositions presently on the market are generally recognized as unsatisfactory, none of them in fact is able to convey to the consumer the characteristic freshness of natural juice.

Somehow, this finding of ours in surprising, especially when considering the efforts put by numerous research teams in the investigation of the aroma of this fruit.

An example of these investigations is represented by the study carried out by Srivas R. Srinivas [see the summary of the communication presented by this author at the Middle Atlantic Regional Meeting of the American Chemical Society, March 1979, Sec. 7] relative to the analysis of the aroma of coldpressed grapefruit peel. This author reported the determining role played by bicyclic sulfury compounds of formulae

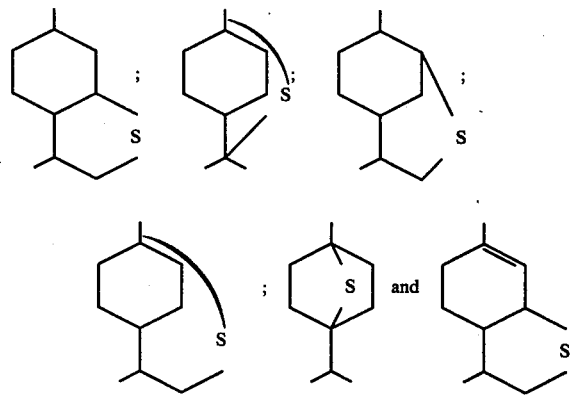

No mention has been made by this author concerning products (I).

The prior art teaches the preparation of allylic mercaptans by means of allyl xanthogenate [see DE-OS 26 15 393] via a process which enables, inter alia, the preparation of a terpenic mercaptan having a structure formally analogous to that of compounds (I). We refer in particular to a compound of formula

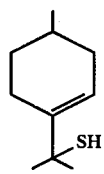

[see compound (40) at page 11 of the cited document]. Though this document discloses, in very broad terms, that the thus obtained allylic mercaptans possess useful odorous properties of flowery and woody type, no specific mention has been made therein about above cited compound (a).

Owing to their organoleptic properties, compounds (I) find a wide utilization in both perfumery and flavours, wherein they contribute to confer, develop and improve the typical odorous and flavouring note of citrus fruits, especially of grapefruit. For instance, they confer freshness to orange or lemon oils by improving their natural character of green fruit.

Surprising and particularly pleasant effects have been observed by the addition of compounds (I) to bergamot oil to which they impart more vitality and strength.

Used in compositions of "eaux fresh" type, they play a very positive role not only towards citrus components but also vis-à-vis jasmin and woody coingredients to which they confer lifting and power.

The proportions at which compounds (I) can be utilized for the manufacture of perfume compositions, bases or concentrates vary in a wide range. However, due to their strength, these proportions are of the order of a few parts per million, based on the weight of the composition, base or concentrate into which they are added.

In the field of flavours, these concentrations can be much lower. Thus marked effects were observed by the use of compounds (I) at concentrations of the order of the ppb, for instance of between about 0.001 and 0.010 ppm.

These values should not be interpreted restrictively. The expert of the art knows in fact that variations in concentration are necessary whenever it is desired to harmonize the different ingredients in a given composition the concentration being dependent on the nature of the articles or foodstuffs it is desired to perfume or flavour.

Compounds (I) can be used either in their isolated form or in admixture with their cyclic derivatives, in particular endo-4,7,7-trimethyl-6-thiabicyclo[3.2.1]octane, with which they interact in a very satisfactory way in most of the applications examined.

We have observed that under certain storage conditions 1-p-menthene-8-thiol converts itself into said cyclisation isomer of formula

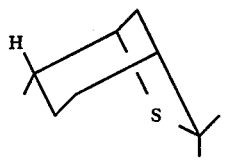

Consequently, it becomes necessary to make use of stabilizers whenever it is wished to increase its shelf-life.

Since one can assume that such a cyclization is eminently due to a radical reaction, suitable stabilizers include for example 3-tert-butyl-4-hydroxy-anisole (BHA), tert-butyl-hydroquinone (TBHQ) or tocopherol.

1-RS-(±)-p-menthene-8-thiol can be prepared according to the process described by Tolstikov [see op. cit.]. Both 1S-(−) and 1R-(+)-enantiomers were prepared in accordance with the following reaction scheme:

Scheme

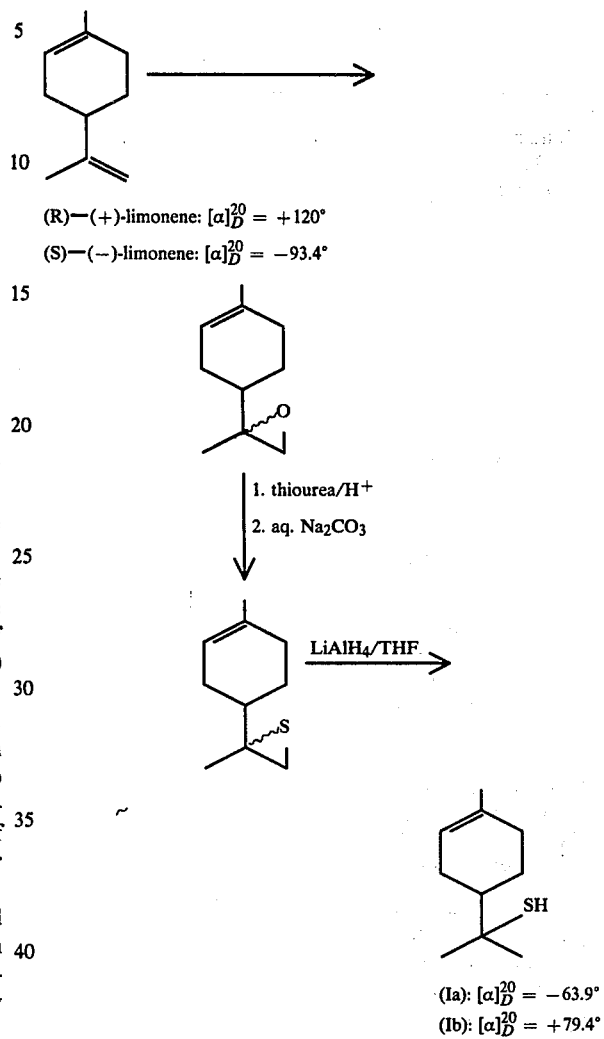

The specific preparation method which was followed is given hereinafter.

(a) 8,9-Epoxy-1-p-menthene 48.5 g (0.5M) of 35% hydrogen peroxide were added dropwise (addition period: 15 min.) to a mixture of
68 g (0.5M) of limonene [R-(+) or S-(−)-limonene]
51.5 g (0.5M) of benzonitrile
12.5 ml of a 0.1M aqueous solution of $Na_2HPO_4$, and
375 ml of methanol.

To the thus obtained mixture there were then added, over 20 min., 12.5 ml of a 0.5M aqueous solution of NaOH (reaction temperature kept at ca. 40° C. by means of external cooling). The reaction was still exothermic during 25 to 40 min. after introduction of NaOH. 5% NaOH in water was then added in order to maintain the reaction mixture at pH 9.5–10.0 (temperature ca. 40° C.). After dilution with water, the reaction mixture was extracted with $CHCl_3$ (3×), washed with 10% $Na_2S_2O_3$ in water (3×), then with 5% KI in water (1×) and finally water, dried over $MgSO_4$ and concentrated under reduced pressure. The obtained residue was treated with petrol ether 30–50, kept 1 hour at room temperature and filtered. After evaporation of the clear filtrate, there were obtained 87.0 g of a mixture of compounds containing the desired epoxide in the proportions of 27%.

An analytical sample was purified by column chromatography (silicagel-toluene/ethyl acetate), b.p. 26° C./0.133 Pa.

IR: 1440, 1175, 910, 840, 790 cm$^{-1}$; MS: M$^+$=152; m/e: 94, 79, 121; NMR (90 MHz): 1.28 (3H, s); 1.65 (3H, s); 1.2–2.3 (7H, m); 2.5–2.70 (2H, m); 5.35 (1H, s)$\delta$ ppm.

(b) 8,9-Epithio-1-p-menthene 2.38 g (15.6 mM) of the epoxide prepared according to letter (a) above were added dropwise, at 5° C. and under nitrogen atmosphere, to a mixture of 1.19 g (15.6 mM) of thio-urea
0.47 ml of H$_2$SO$_4$, and
5.47 ml of water.

The thus obtained mixture was stirred 15 min. at ca. 0° C., then 14 hours at room temperature. After dilution with 60 ml of water, 1.66 g (15.6 mM) of Na$_2$CO$_3$ in 8.6 ml of water were added dropwise to the above mixture (addition period: 1 hour). After stirring during 20 min. at 25° C., then 25 min. at 50° C., the reaction mixture was extracted with pentane (3×), washed with water (3×), dried and evaporated. After distillation of the crude material, there were obtained 1.44 g (54% yield) of the desired compound, b.p. 40° C./0.133 Pa.

IR: 1430, 1375, 1150, 1055, 915, 785–800 cm$^{-1}$; MS: M$^+$=168; m/e: 68; NMR (90 MHz): 1.52 (3H, s); 1.66 (3H, s); 1.2–2.2 (7H, m); 2.30–2.50 (2H, m); 5.35 (1H, s)$\delta$ ppm.

(c) 1-p-Menthene-8-thiol 0.637 g (3.8 mM) of the compound prepared according to letter (b) above in 12 ml of tetrahydrofuran (THF) were added under nitrogen atmosphere to a stirred boiling suspension of 72 mg (1.9 mM) of LiAlH$_4$ in 3 ml of THF. The reaction mixture was refluxed for 1 further hour, then cooled at 0° C. and the excess of LiAlH$_4$ decomposed by addition of water. The obtained mixture was then extracted with ether (3×) and the organic phase washed with water (3×), dried and evaporated. After fractional distillation of the crude residue, there were obtained 0.450 g (69% yield) of the desired 1-p-menthene-8-thiol, b.p. 40° C./0.133 Pa.

IR: 1440, 1380, 1360, 1155, 1120 and 795 cm$^{-1}$; NMR (90 MHz): 1.35 (3H, s); 1.40 (3H, s); 1.56 (1H, s); 1.66 (3H, s); 1.2–2.2 (7H, m); 5.35 (1H, m)$\delta$ ppm.

In the description of the above process, temperatures are indicated in degrees centigrade and the abbreviations have the meaning common in the art.

As stated above, in the field of flavours, the sulfur containing terpenes of the invention are particularly suited to the reconstitution of the characteristic aroma and taste of grapefruit. However, their gustative properties are such that one can envisage a much broader use of them. Due to their fresh and lifting fruity note, compounds (I) can find a utilization to enhance the natural character of fruit juices such as apricot, peach, passion fruit or black-currant juice. They can be used also to aromatize beverages of different nature, infusions or decoctions for example, or non-nutritive beverages like dietary beverages or even articles for mouth-cleaning. They impart also aromatic pleasant characters to chewing-gums, candies, confectionary products and tobacco.

Though the organoleptic properties of the different compounds of formula (I) are very similar, we have observed that (S)-(−)-1-p-menthene-8-thiol possessed a more fruity and less sulfury note than its (R)-(+)-enantiomer. Their utilization range however is analogous.

The invention is better illustrated by but not limited to the following examples.

EXAMPLE 1

3.0 g of commercial grapefruit oil were used for flavouring 10.0 l of an acidulous sugar syrup (prepared from 6 kg of cane sugar, 10 l of water and citric acid, this latter ingredient being added in the proportions of 0.2%). Racemic 1-p-menthene-8-thiol was then added to two samples of the above flavoured syrup, in the proportions of 0.002 and 0.005 ppm, respectively.

After tasting, it was declared that the resulting beverages presented a more lifting and more juicy character, reminiscent of the particular flavour of natural grapefruit juice.

Quite similar results were observed when racemic 1-p-menthene-8-thiol was replaced by one of the enantiomers of formula (Ia) and (Ib).

EXAMPLE 2

Various samples of commercial fruit juices were flavoured with 1-p-menthene-8-thiol, in the proportions given in the table hereinafter. The evaluation comments of the panel of flavour experts are summarized as follows.

| Flavoured material | Dosage (ppb) | Evaluation comments |
| --- | --- | --- |
| Apricot juice | 1–2 | fresher, smoother |
| Peach juice | 1–2 | more lifting, fresher |
| Passion fruit juice | 2–3 | fresher, more juicy, more typical |
| Black-currant juice | 1–2 | more juicy, fresher, more typical. |

EXAMPLE 3

A mint-type base flavouring composition was prepared by mixing the following ingredients:

| Ingredients | Parts by weight |
| --- | --- |
| Peppermint oil | 800 |
| Orange oil | 100 |
| Grapefruit oil | 50 |
| Anise oil | 50 |

Test flavour (A) and control flavour (B) were then prepared by adding 10 g of a 10% solution of the mint-type base in 95% ethyl alcohol to 100 l of diluted sugar syrup. Test flavour (A) was then flavoured with 1-p-menthene-8-thiol, in the proportions of 2–4 ppb. After tasting, it was declared that the aroma of the thus flavoured syrup was more lifting and more herbal than that of control flavour (B).

EXAMPLE 4

A base perfume composition was prepared as indicated hereinafter.

| Ingredients | Parts by weight |
| --- | --- |
| Synthetic bergamot oil | 200 |
| Mandarin oil | 50 |
| Mandarin aldehyde 10%*[1] | 5 |
| Lavandin oil | 50 |
| MYROXYDE ®[1] | 5 |
| Synthetic citronellol | 50 |
| Hexyl-cinnamic aldehyde | 50 |

-continued

| Ingredients | Parts by weight |
| --- | --- |
| Hydroxycitronellal | 100 |
| MAYOL ®[1] | 10 |
| Synthetic oak moss 10%* | 50 |
| Cetyver[1] | 50 |
| Jonquil oil 10%* | 10 |
| HEDIONE ®[1] | 50 |
| GALAXOLIDE ®[2] | 50 |
| Musc DTI[1] | 50 |
| 1-p-Menthene-8-thiol at 1°/₀₀* | 15 |
| Total | 795 |

*in ethyl citrate
[1]Origin: FIRMENICH SA, Geneva-Switzerland
[2]Origin: Intern. Flavors & Fragrances, USA Due to the addition of 1-p-menthene-8-thiol, the above composition acquired a more powerful and more lifting odour.

What we claim is:

1. The method for enhancing, improving or modifying the fruity organoleptic properties of foodstuffs, beverages and chewing-gums which comprises the step of adding thereto a flavoring effective amount of 1-p-menthene-8-thiol in its racemic or enantiomeric form.

2. Method according to claim 1, wherein the beverage is based on natural grapefruit or a grapefruit imitating composition.

3. Method according to claim 1, wherein 1-p-menthene-8-thiol is used at a concentration of between about 0.001 and 0.010 parts per million by weight.

* * * * *